United States Patent [19]
Russell

[11] Patent Number: 5,741,663
[45] Date of Patent: Apr. 21, 1998

[54] **SELECTIVE ADDITIVE AND MEDIA FOR *PSEUDOMONAS FLUORESCENS***

[75] Inventor: Scott Marshall Russell, Athens, Ga.

[73] Assignee: University of Georgia Research Foundation, Inc., Athens, Ga.

[21] Appl. No.: 632,929

[22] Filed: Apr. 16, 1996

[51] Int. Cl.⁶ .................................................. C12Q 1/04
[52] U.S. Cl. ........................... 435/34; 435/4; 435/29
[58] Field of Search ........................ 195/103.5; 435/34, 435/29, 4, 7.2, 30

[56] References Cited

U.S. PATENT DOCUMENTS

| | | | |
|---|---|---|---|
| 3,284,362 | 11/1966 | Zussman | 252/107 |
| 3,405,184 | 10/1968 | Widiger, Jr. et al. | 260/613 |
| 3,506,720 | 4/1970 | Model et al. | 260/613 |
| 3,616,256 | 10/1971 | Furia | 195/103.5 |
| 3,642,872 | 2/1972 | Model et al. | 260/479 |
| 3,784,694 | 1/1974 | Model et al. | 424/304 |
| 3,904,696 | 9/1975 | Model et al. | 260/613 |
| 5,447,849 | 9/1995 | Toora | 435/34 |

OTHER PUBLICATIONS

DIFCO Laboratories Manual, Tenth Edition, "Dehydrated Culture Media and Reagents for Microbiology"; 711–712 (1984).
Schiemann, D.A. (1979) *Can. J. Microbiol.* 25:1298–1304; "Synthesis of a selective agar medium for *Yersinia enterocolitica*".
Furia and Schenkel (1968) *Soap and Chemical Specialties* Jan: 47–50, 116, 118, 120, 122.
Mead and Adams (1977) *Br. Poultry Sci.* 18:661–670.
Cousin et al (1992) Compendium of Methods for the Microbiological Examination of Foods, C. Vanderzant and D.F. Splittstoesser, ed. American Public Health Association, Washington, DC 156–157.
Bishop et al (1984) *J. Food Prot.* 47:471–475.
Barnes and Thornley (1966) *J. Food Technol.* 1:113–119.
Firstenberg–Eden and Tricarico (1983) *J. Food Sci.* 48:1750–1754.
Prepared Foods (1988) 157:118.
Ogden, I.D. (1986) *J. Appl. Bacteriol.* 61:263–268.
Halleck et al. (1957) *Food Technol.* 12:197–203.
Ayres et al. (1950) *Food Technol.* 4:199–205.
Haines, R.B. (1937) Dept. Sci. Ind. Research Food Invest. Board (Gr.Brit) Special Report No. 45, London: H.M.S.O.; pp. 35–38.
Kirsch et al. (1952) *Food Res.* 17:495–503.
Lockhead and Landerkin (1935) *Sci. Agr.* 15:765–770.
Wolin et al. (1957) *Food Res.* 22:682–686.
Viehweg et al. (1989) *Lebensm.–Wiss. u.–Technol.* 22:356–367.
Power and McCuen (1988) *Manual of BBL Products and Laboratory Procedures* Beckton Dickinson Microbiology Systems, Cockeysville, Maryland, 227–228.
Atlas, R.M. (1995) *Handbook of Microbiological Media for the Examination of Food* CRC Press, Inc. Boca Raton, Ann Arbor, London, Tokyo, p. 173.
Lorian, V. (1980) *Antibiotics in Laboratory Medicine* Williams and Wilkins, Baltimore, MD London, U.K. 623–687.
Easter et al. (1982) *J. Appl. Bacteriol.* 53:357–365.
Fitz–Gerald and Deeth (1983) *Austrl. J. Dairy Technol.* 38:97–103.
Frieden, C. (1971) *Ann Rev. Biochem.* 40:653–696.
Hankin and Dillman (1968) *J. Milk Food Technol.* 31:141–145.
Pooni and Mead (1984) *Food Microbiol.* 1:67–68.
White and Little (1983) *J. Dairy Sci.* 66:268, Abstract.
Cox et al. (1981) *Poultry Sci.* 60:768–770.
Russell et al. (1996) *Poultry Sci.* 75:2041–2047.
Russell et al. (1995) *Poultry Sci.* 74:81 (Suppl.1), Abstract.
Russell et al. (1995) *J. Food Protection* 58:1124–1128.
Shaw et al., "A Study of the relative Incdence of Different Identification technique employing only carbon source tests," J. of Applied Bacteriology Aug. 1984, 57, 59–67.
Ogden et al., "Use of conductance methods to predict bacterial counts in Fish," Jul. 1986, 61, 263–268.

*Primary Examiner*—John Kight
*Assistant Examiner*—Dameron Jones
*Attorney, Agent, or Firm*—Greenlee, Winner and Sullivan, P.C.

[57] ABSTRACT

The present invention provides methods and compositions for the specific detection of *Pseudomonas fluorescens* and for the selective growth of this bacterium. In a preferred embodiment, selective growth of *P. fluorescens* is effected by the combination of Irgasan, carbenicillin and nitrofurantoin in a bacteriological medium comprising suitable nutrients for its growth. Also provided is a fast, reliable and economical method for the assessment of microbial quality of a fresh animal product, such as poultry, beef, fish, shellfish, milk or the like, using media selective for the growth of *P. fluorescens* and detection methods for microbial growth in the selective media.

13 Claims, No Drawings

1

SELECTIVE ADDITIVE AND MEDIA FOR *PSEUDOMONAS FLUORESCENS*

The present invention was made, at least in part, with Hatch Act funding. Accordingly, the United States Government may have certain rights in this invention.

FIELD OF THE INVENTION

The field of the present invention is in the area of media additives selective for specific bacterial species, particularly *Pseudomonas fluorescens*, and methods for determining microbial quality and estimating potential shelf-life of certain foods using same.

BACKGROUND OF THE INVENTION

Fresh, unprocessed foods, specifically proteinaceous foods such as poultry, meat, fish, shellfish and milk, are perishable, and there is a defined potential shelf-life (time required for spoilage defects to become organoleptically detectable) for these foods.

Spoilage occurs when certain species of psychrotrophic bacteria multiply on the surface of poultry, beef, pork, fish, or in milk held at refrigeration temperatures and produce metabolic by-products that change the appearance, texture, or odor of the product. These by-products depend on the energy source available to the bacteria. During the first few days after processing, psychrotrophic bacterial populations utilize glucose or other carbohydrates as their primary source of energy. Generally, the by-products of glucose metabolism do not substantially contribute to spoilage defects in proteinaceous foods; however, as glucose is depleted, spoilage bacteria utilize other substrates, such as amino acids, that are present in skin and muscle. Amino acid metabolism produces odorous end products that make foods unacceptable [Pooni and Mead (1984) *Food Microbiol.* 1:67–78].

The spoilage rate of fresh foods depends on the initial number of spoilage bacteria on or in the product immediately after processing. Because psychrotrophic bacteria originate from the environment, the outer surface of the animal, the water supply, chill tank, and equipment in the processing plant [Barnes, E. M. (1960) *Soc. Health Journal* 80:145–148], the initial number of spoilage bacteria on foods varies greatly depending on processing parameters. Enumeration of spoilage bacteria on fresh poultry, beef, pork, fish, and in milk and the like, may be used to determine processing sanitation efficiency, and fast, easy and inexpensive methods are needed to enumerate spoilage bacteria before storage and/or shipment of product.

Another factor that affects spoilage rate is the holding temperature of the product during storage, transport, and retail display. Following processing and throughout distribution and marketing, opportunities exist for fresh foods of animal origin to be exposed to temperature mishandling [Russell et al. (1994) *Poultry Sci.* 73:739–743]. Fresh foods that do not meet their expected potential shelf-life can be assumed to have been exposed to temperature abuse or subsequent contamination. Hence, a potential shelf-life prediction method may also be useful for identifying cases of temperature or other abuse.

Methods for predicting potential shelf-life of fresh fish and milk have been developed. Total aerobic plate counts have been used, but plate counts have been considered of limited value in predicting the keeping quality of milk [Fitz-Gerald and Deeth (1983) *Austral. J. Dairy Technol.* 38:97–103; Frieden, C. (1971) *Ann. Rev. Biochem.* 40:653–660; Hankin and Dillman (1968) *J. Milk Food Technol.* 31:141–145; Hankin and Anderson (1969) *J. Milk Food Technol.* 32:49–51; Hankin and Stephens (1972) *J. Milk Food Technol.* 35:574–576; Janzen et al. (1982) *J. Dairy Sci.* 65:2237–2240; Law, B. A. (1979) *J. Dairy Res.* 46:573–588; Marth, E. H. (ed.) (1978) 14th ed. Am. Publ. Health Assoc., Washington, D.C., p. 77; Mayerhofer et al. (1973) *Appl. Microbiol.* 25:44–48; Patel and Blankenagel (1972) *J. Milk Food Technol.* 35:203–206; Punch et al. (1966) *J. Dairy Sci.* 48:1179–1183; Randolph et al. (1965) *J. Milk Food Technol.* 28:92–96]. Psychrotrophic plate counts, which require an incubation period of 7 d at $10°\pm1°$ C. [Cousin et al. (1992) in: Compendium of Methods for the Microbiological Examination of Foods. C. Vanderzant and D. F. Splittstoesser, ed. American Public Health Association, Washington, D.C., p. 156–157], have also been used as a general indicator of potential shelf-life; however, enumeration of psychrotrophic spoilage bacteria using this technique is difficult, cumbersome, and time consuming. Often, fresh animal-derived foods have been purchased and consumed or have spoiled before populations of psychrotrophic bacteria can be enumerated.

An impedance method was developed to determine the potential shelf-life of pasteurized whole milk; however, the assay described by Bishop et al. [Bishop et al. (1984) *J. Food Prot.* 47:471–475] uses an incubation temperature of 18° or 21° C. and a nonselective growth medium. A previous study [Firstenberg-Eden and Tricarico (1983) *J. Food Sci.* 48:1750–1754] indicated that, at 18° and 21° C., the generation time of *E. coli* is less than the generation time for *Pseudomonas* spp. For samples containing mixed microflora, such as a broiler chicken carcass, where mesophilic bacteria represent 92% of the initial flora [Barnes and Thornley (1966) *J. Food Technol.* 1:113–119], mesophilic bacteria rather than psychrotrophic bacteria are preferentially enumerated at 18° or 21° C. Bishop, et al. (1984) *J. Food Prot.* 47:471–475 reported high correlation coefficients (0.87 and 0.88) between the shelf-life of milk and impedance readings taken at 18° and 21° C., respectively; however, at 18° and 21° C., mesophilic species on chickens are enumerated instead of psychrotrophs using impedance unless a selective medium is used.

Another method described in *Prepared Foods* (1988) 157:118 involves the use of impedance to measure total mesophilic populations of bacteria on broiler chicken to predict the shelf-life of fresh poultry. While mesophiles may be a general indicator of the overall microbial quality of the carcass, they are not the bacteria responsible for spoilage of fresh poultry. Huss et al. [Huss et al. (1974) *J. Food Technol.* 9:213–221] reported that total viable count is a very poor indicator of both quality and shelf-life of fresh fish. Jørgenson et al. [Jørgenson et al. (1988) *J. Food Microbiol.* 6:295–307] stated that a count of the specific organisms involved in fish spoilage should be more useful than total viable count in predicting remaining shelf-life.

A conductance method for determining the potential shelf-life of fresh fish was developed by Ogden (Ogden, I. D. (1986) *J. Appl. Bacteriol.* 61:263–268]. Conductance measurements on fresh fish were carried out using nutrient broth, brain heart infusion broth, sea water broth, and modified trimethylamine oxide medium (Wood and Baird (1943) *J. Fisheries Board Can.* 6:194–201) with NaCl and fish broth added [Ogden, I. D. (1986) *J. Appl. Bacteriol.* 61:263–268]. Conductance measurements using brain heart infusion broth at 20° C. correlated well ($R^2$=0.92 to 0.97) to $H_2S$ producing bacterial counts; however, at 20° C., mesophilic bacterial populations, not Pseudomonas, would be enumerated using electrical measurements on samples taken from fresh chicken.

What is needed is a means to predict the potential shelf-life of fresh foods of animal origin, preferably by rapidly enumerating the populations of bacteria that are primarily responsible for producing spoilage defects in these products immediately after processing. Barnes and Thornley (1966) *J. Food Technol.* 1:113–119 observed that *Pseudomonas* spp. make up only 2% of the initial flora of broiler chicken carcasses. Halleck et al. (1957) *Food Technol.* 12:197–203 reported that immediately after processing, *Pseudomonas fluorescens* seldom exceeded 5% of the bacterial population on fresh meats. Pseudomonas and Shewanella (formerly classified as Pseudomonas or Alteromonas) have been reported as the primary spoilers of fresh poultry since the 1930s (Ayres et al. (1950) *Food Technol.* 4:199– 205; Empey and Scott (1939) *Commonwealth Aust. Court. Sci. Ind. Res. Bull.* 126; Haines, R. B. (1937) Dept. Sci. Ind. Research Food Invest. Board (Gr. Brit.) Special Report No. 45. London: H.M.S.O.; Kirsch et al. (1952) *Food. Res.* 17:495–503; Lockhead and Landerkin (1935) *Sci. Agr.* 15:765–770; Wolin et al. (1957) *Food Res.* 22:268–288]. Viehweg et al. (1989) *Lebensm.-Wiss. u.-Technol.* 22:356–367 observed that the pseudomonads and Shewanella produced more sulfur compounds than any of the other common spoilage bacteria, and that these sulfur compounds masked other less odoriferous volatiles during subjective odor evaluations. Halleck et al. (1957) *Food Technol.* 12:197–203 reported that *Pseudomonas fluorescens* constituted approximately 80% of the bacterial species on meat in the latter part of storage. Russell et al. (1995) *Poultry Sci.* (In press) reported that the bacteria isolated from spoiled broiler chicken carcasses that produced sulfur off-odors in chicken skin medium were *Pseudomonas fluorescens* A, B and D, *fragi*, and *putida*) and *Shewanella putrefaciens* A, B and D. Other studies have shown that *P. fluorescens* is an important spoilage organism of milk. Therefore, any potential shelf-life prediction method should effectively enumerate *Pseudomonas fluorescens* because it is most commonly associated with objectionable spoilage defects on foods of animal origin.

An accurate, fast and economical method for determining the potential shelf-life of fresh poultry, meats, fish, shellfish and milk is needed for determining: 1) potential shelf-life under ideal holding conditions; 2) general processing sanitation; and 3) exposure of the product to temperature abuse. If processing sanitation is inadequate, a lower potential shelf-life would be predicted on carcasses analyzed at Day 0. Where the foregoing fresh products do not meet their expected shelf-lives, it can be concluded that they were temperature abused or contaminated after monitoring.

SUMMARY OF THE INVENTION

The present invention provides a Pseudomonas Selective Additive (PSA) for incorporation into a bacteriological growth medium, where that selective additive allows the growth of *Pseudomonas fluorescens* while inhibiting the growth of other bacterial species. The PSA of the present invention comprises nitrofurantoin, carbenicillin and a compound of the formula

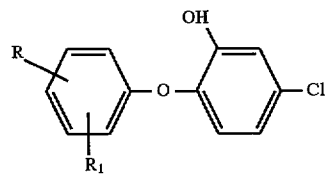

wherein R is halogen and $R_1$ is hydrogen or chlorine, from about 1 to about 800 mg per liter, all as prepared in bacteriological medium. Exemplary compounds fitting the given formula include, but are not limited to, 2-hydroxy-4,4'-dichlorodiphenyl ether, 2-hydroxy-4-chloro-4'-bromodiphenyl ether, 2-hydroxy-3',4,4'-trichlorodiphenyl ether, 2-hydroxy-2',4,4'-trichlorodiphenyl ether and the like.

The PSA of the present invention preferably contains 2,4,4'-trichloro-2'-hydroxydiphenyl ether (Irgasan DP300), carbenicillin and nitrofurantoin; for one liter of bacteriological medium the PSA contains from about 1 mg to about 50 mg Irgasan, from about 5 mg to about 200 mg carbenicillin and from about 1 mg to about 200 mg nitrofurantoin; preferably about 25 mg to about 30 mg Irgasan, about 120 mg to about 130 mg carbenicillin and from about 3 mg to about 20 mg nitrofurantoin; most preferably 25 mg Irgasan, 120 mg carbenicillin and 4 mg nitrofurantoin. Optionally, other additives including, without limitation, salts and trimethylamine oxide (TMAO), can also be present as further selective agents.

The PSA of the present invention can be sold in dry form for reconstitution in absolute ethyl alcohol and filter sterilization before addition to tempered, sterile bacteriological growth medium. For addition to one liter of medium, the PSA preferably contains 4 mg nitrofurantoin, 120 mg carbenicillin and from 100 to 800 mg of a compound of the formula

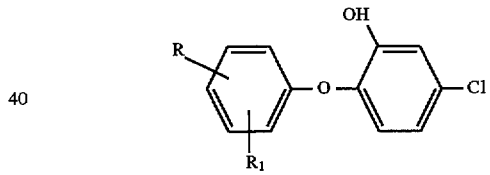

where R is a halogen and $R_1$ is H or Cl. Preferably R and $R_1$ are Cl. As contemplated herein, the PSA dry composition in the mount for one liter is dissolved in about 1 to about 5 ml, preferably 1 ml, 100% ethanol and filter-sterilized (0.2 μm pore-size filter) before use. It is understood that amounts can be varied as long as the end concentration in the medium is maintained.

Another aspect of the present invention is a method for assessing the microbial quality of an animal product, preferably at or immediately after the processing as a fresh animal product, comprising the steps of 1) sampling the product for bacterial content, for example, by rinsing a sample of product with suitable sterile diluent such as deionized water, phosphate buffered saline or 0.85% saline to produce a product wash fluid;

2) inoculating a measured volume of the product wash fluid of step 1) into a bacteriological growth medium containing PSA to produce inoculated growth medium containing PSA;

3) incubating the inoculated growth medium containing PSA at a temperature from about 0° C. to about 30° C., preferably at about 25° C. for from 1 hr to about 48 hrs; and 4) determining turbidity in the medium incubated in step 3), whereby turbidity is an indication of growth of Pseudomonas fluorescens.

The method can include the step of diluting and plating the medium to estimate viable cell count at the beginning and/or end of the incubation period. Alternatively, or in addition to the determination of viable cell count, aliquots of the inoculated medium can be assessed for changes in impedance or capacitance relative to the inoculated medium at the time of inoculation (before incubation) or relative to an aliquot of uninoculated (sterile) medium containing PSA which was incubated in parallel to the inoculated medium. Preferably the uninoculated control medium contains an equivalent proportion of sterile diluent as the inoculated medium. A change in impedance detection time or in capacitance detection time is indicative of the growth of Pseudomonas fluorescens. The initial P. fluorescens viable cell count can be estimated with reference to time of incubation required to achieve a measurable change in medium capacitance or impedance and to parameters determined for the particular growth medium and incubation temperature.

DETAILED DESCRIPTION OF THE INVENTION

As described in Example 1, the number of isolates recovered from broiler chicken carcasses obtained from the chiller exit of a commercial processing plant and analyzed using capacitance at Day 0 using brain heart infusion (BIB) broth with 25 µg Irgasan/ml, (BHI-I) as the culture medium is presented in Table 1. Irgasan was added to BHI because Furia and Schenkel [Furia and Schenkel (1968) *Soap and Chemical Specialties Jan:* 47–50,116,118,180,122] demonstrated that it selects for the growth of *Pseudomonas* spp. while suppressing the growth of other bacteria. Irgasan at a level of 25 µg/mL is also used as the selective agent in Pseudomonas Isolation Agar (Difco Laboratories, Detroit, Mich.). Power and McCuen [Power and McCuen (1988) *Manual of BBL® Products and Laboratory Procedures* Becton Dickinson Microbiology Systems, Cockeysville, Md. 227–228] reported that Irgasan selectively inhibits Gram-positive and Gram-negative bacteria; however, *Pseudomonas* spp. are resistant to the microbial compound.

Electrical methods for detection of microbial (e.g., bacterial) growth include measurements of capacitance, impedance or conductance during incubation. Typically, the threshold cell density for detecting growth-dependent electrical changes in a culture is about $10^6$ cells per mL, and typically, a plot of an electrical parameter such as conductance or capacitance versus incubation time results in a line with a breakpoint at about the time the cell density in the culture reaches about $10^6$ per mL. In general, capacitance and conductance increase as cell density increases, while impedance drops as cell density increases. Changes in these electrical parameters of the culture are due to bacterial metabolism and the concomitant changes in electrolyte concentrations in the medium, for example the production of acids from a complex neutral carbohydrate or neutral sugar, and/or production of acids from complex proteinaceous material such as peptides or proteins. A bacterial growth medium suitable for such electrical methods is one where bacterial growth and metabolism has a strong impact on electrolyte composition. As specifically exemplified, brain heart infusion broth (Difco Laboratories, Detroit, Mich.) allows good sensitivity for measurement of microbial growth by electrical methods including capacitance. impedance or conductance as a function of incubation time, and therefore, cell growth and cell concentration.

Using BHI-I, cultures of *Pseudomonas fluorescens, Pseudomonas putida, Aeromonas sobria, Aeromonas salmonicida salmonicida, Aeromonas hydrophila caviae, Vibrio alginolyticus,* and *Serratia liquefaciens* were each able to reach the threshold level of $10^6$ cells/mL at the time of detection and thus, were able to change the capacitance of the medium sufficiently to be detected by the Bactometer.

*Pseudomonas fluorescens* is one of the three most predominantly isolated spoilage bacteria associated with fresh poultry [Russell et al. (1995) *Poultry Sci.* (In press), and Viehweg et al. (1989) *Lebensm.-Wiss. u.-Technol.* 22:356–367]. Viehweg et al. reported that the pseudomonads and Shewanella produced more sulfur compounds than other spoilers. These sulfur compounds were able to mask other less odiferous volatiles during subjective odor evaluations. *P. fluorescens* and *P. putida* reportedly made up 50% of the spoilage flora by the eighth day of storage and remained detectable at all stages of spoilage.

*Pseudomonas fluorescens* was one of seven species selectively enumerated using BHI-I. Therefore, three other basal media and BHI-I containing various antimicrobial compounds and chemicals were analyzed to determine which combination could be used to suppress the growth of other bacteria and allow only *Pseudomonas fluorescens* to reach the threshold level.

Cephaloridine, fucidin, cetrimide (CFC) medium was developed by Mead and Adams (1977) *Br. Poultry Sci.* 18:661–670 to rapidly isolate pigmented and nonpigmented pseudomonads. The authors reported that CFC medium supported the growth of *Pseudomonas aerugenosa,* an organism which is not involved in poultry spoilage. Forty-one percent of the bacteria isolated from swabs taken from poultry carcasses using CFC medium were non-pseudomonads, including *Acinetobacter/Moraxella* spp., 3%, Enterobacteriaceae, 8%, *Alcaligenes* spp., 2%, *Flavobacterium* spp., 8%, Gram-positive unclassified, 4%, and Gram-negative unclassified, 16% [Mead and Adams (1977) *Br. Poultry Sci.* 18:661–670]. Because several interfering genera were able to grow on CFC agar, it was eliminated as a possible medium for rapid enumeration of *Pseudomonas fluorescens*.

Maleate medium for *Pseudomonas fluorescens* (without agar added) [Atlas, R. M. (1995) *Handbook of Microbiological Media for the Examination Food* CRC Press, Inc., Boca Raton, Ann Arbor, London, Tokyo, p. 173] was analyzed to determine its suitability for use in capacitance assays. Pure cultures of *P. fluorescens* were not able to multiply in this medium as no detection times were recorded. When analyzing broiler carcass rinses using this medium, detection times were erratic and the instrument was unable to interpret the capacitance curves consistently. Maleate medium was thus considered unsuitable for conducting capacitance assays for *P. fluorescens*.

Growth of bacteria isolated using BHI-I in PIM-AGAR (Pseudomonas isolation medium without agar) is presented in Table 2. PIM-AGAR was not more selective than BHI-I for the growth of *P. fluorescens* as all competing flora isolated using BHI-I were able to multiply. Thus, PIM-AGAR is not suitable for enumerating *P. fluorescens* using capacitance.

Ampicillin, carbenicillin, cephalothin, chloramphenicol, and nitrofurantoin were chosen as inhibitors to select for the growth of *P. fluorescens* because Lorian [Lorian, V. (1980) *Antibiotics in Laboratory Medicine* Williams and Wilkins, Baltimore, Md., London, U.K., 623–687] reported that *P. fluorescens* were resistant to these compounds and the other species of bacteria listed in Table 1 were susceptible to them. NaCl and TMAO were used to enhance capacitance readings as previously described by Easter et al. (1982) *J. Appl. Bacteriol.* 52:357–365.

Data for growth of bacteria in BHI with various levels of Irgasan, chloramphenicol, cephalothin, carbenicillin, NaCl, and trimethylamine N-oxide (TMAO) and TMAO medium are presented in Table 3. The bacteria were initially isolated using BHI+I. None of these media sufficiently selected for the growth of *P. fluorescens*, while suppressing the growth of the other species tested, to be suitable for enumerating *P. fluorescens*.

Data for growth of bacteria in BHI with various levels of Irgasan, ampicillin, cephalothin, carbenicillin, NaCl, and trimethylamine N-oxide (TMAO) are presented in Table 4. The bacteria were initially isolated using BHI+I. Although *Pseudomonas fluorescens* grew well in the media analyzed, *A. sobria*, *A. salmonicida salmonicida*, *A. hydrophila caviae*, *V. alginolyticus*, and *S. liquefaciens* also grew. None of these media was appropriate for selecting for *P. fluorescens*.

Data for growth of bacteria in BHI with various levels of cephalothin, carbenicillin, NaCl, and trimethylene N-oxide (TMAO) are presented in Table 5. The bacteria were initially isolated using BHI+I. Although *P. fluorescens* grew well in three of the media analyzed, *Aeromonas sobria* was able to produce higher turbidity in those media. Thus, these media were not suitable for enumerating *P. fluorescens*.

Data for growth of bacteria in General Purpose Medium Plus (GPMP) with various levels of cephalothin, carbenicillin, NaCl, and trimethylamine N-oxide (TMAO) are presented in Table 6. The bacteria were initially isolated using BHI+I. None of these media permitted *P. fluorescens* to multiply rapidly enough to be used in a capacitance assay.

Data for growth of bacteria in BHI with various levels of nitrofurantoin, carbenicillin, Irgasan and trimethylamine N-oxide (TMAO) are presented in Table 7. The bacteria were initially isolated using BHI+I. Seven of the eight media analyzed allowed *P. fluorescens* to multiply while suppressing the growth of the other bacterial isolates. BHI with nitrofurantoin (25 µg), carbenicillin (80 µg), Irgasan (25 µg), TMAO (1 mg) per mL of medium was the most selective. The tubes containing this medium and *P. fluorescens* had a maximum of 20% less transmittance than the other bacterial isolates analyzed.

Data for growth of bacteria in BHI with various levels of nitrofurantoin, carbenicillin, Irgasan and trimethylamine N-oxide (TMAO) are presented in Table 8. The bacteria were initially isolated using BHI+I. BHI containing nitrofurantoin (3 µg), carbenicillin (80 µg), Irgasan (5 µg) per mL of medium was the most selective medium. The tubes containing this medium and *P. fluorescens* had a maximum of 24% less transmittance than the other bacterial isolates analyzed. This medium did not contain TMAO. Hence, TMAO was not included in the medium to be used for capacitance assays. Although this medium was excellent for selecting for the growth of *P. fluorescens* while suppressing the growth of the other isolates analyzed, the amount of Irgasan in the medium is probably not sufficient to suppress the growth of other Gram-negative bacteria commonly associated with broiler chicken rinses. Therefore, a similar medium containing 25 µg/mL Irgasan that was used to obtain the seven isolates listed in Table 1, was investigated. Nitrofurantoin and carbenicillin concentrations were increased to insure the control of competing flora.

Data for growth of bacteria in brain heart infusion broth with nitrofurantoin, Irgasan, and decreasing levels of carbenicillin are presented in Table 9. The bacteria were initially isolated using BHI+I. *Aeromonas sobria* was able to proliferate at carbenicillin levels below 120 µg/mL. Therefore, reduction of carbenicillin is not possible when selecting for growth of *P. fluorescens*.

Data for growth of bacteria in BHI with the following additives per mL of medium: nitrofurantoin (4 µg), carbenicillin (120 µg), Irgasan (25 µg) are presented in Table 10. The bacteria were initially isolated using BHI+I. This medium was considered "ideal" because it contained high levels of antibiotic while allowing for rapid proliferation of *P. fluorescens*. This medium was named BHI-PSA and was used for capacitance assays.

The number of isolates recovered from broiler chicken carcasses analyzed using capacitance at Day 0 or after holding at 3° C. for 3, 6, 9, 12 or 15 d using BHI-PSA as the culture medium is presented in Tables 11–16. On Day 0 (Table 11), for 4 of the 6 carcasses analyzed, *P. fluorescens* was the bacterium that reached the capacitance detection threshold first. For the other 2 carcasses, *P. putida* was responsible for changing the capacitance of the medium to the extent that the instrument could detect the change. Only one other species of bacteria was isolated from the plates at high dilutions. For plates on which bacterial species other than *P. fluorescens* were isolated, that plate was examined to determine the bacterium that was overwhelmingly predominant on that plate and thus, would be the organism that produced the impedance change detected by the instrument. *P. fluorescens* was the overwhelmingly predominant species on the Day 0 viable cell count plate that contained an unidentified bacterial isolate termed CDCEF-4. Overall, *P. fluorescens* was the bacterium that was selectively enumerated on Day 0 carcasses. Results presented in Table 9 and 10 indicate that *P. putida* is unable to multiply in the BHI-PSA medium.

For 5 of 6 carcasses held for 3 days at 3° C. (Table 12), *P. fluorescens* was the bacterium that reached $10^6$ first and, hence, was responsible for the capacitance reading. One bacterial species other than *P. fluorescens* was isolated from the viable cell count plates at high dilutions; however, the overwhelmingly predominant species on such plates was *P. fluorescens*.

On carcasses held for 6, 9, 12 and 15 days (Tables 13, 14, 15 and 16), for all samples, *P. fluorescens* was responsible for changing the capacitance of the medium to the extent that the instrument could detect the change. Although other species of bacteria (*Flavobacterium meningosepticum*, *Aeromonas hydrophila caviae*, Gram-negative bacilli, *Alcaligenes* spp., *Chromobacterium violaceum*, and CDC EF-4) were isolated at high dilutions, the predominant species on those plates was *P. fluorescens*. In most cases only one colony of these contaminants was visually apparent on plates at these dilutions.

BHI containing nitrofurantoin (4 µg), carbenicillin (120 µg), and Irgasan (25 µg) per mL was excellent for enumeration of *P. fluorescens* from broiler chicken carcass rinses using capacitance microbiology at 25° C. The average times required to enumerate *P. fluorescens* Day 0, 3, 6, 9, 12 and 15 samples were 22.4, 17.2, 12.0, 4.6, 2.9 and <1.0 h respectively. This procedure is rapid, easily performed, and is a useful tool for determining the number of spoilage bacteria on fresh chicken and other animal food products including milk, meat, poultry, fish and shellfish. Thus it can be used to predict the potential shelf-life of fresh chicken and other foods of animal origin.

The following discussion is provided in reference to the experiments described in Example 2 hereinbelow. Total psychrotrophic plate counts (PPC)±standard error of the mean (SEM) for broiler chicken carcasses analyzed immediately (Day 0), or sampled after holding at 3° C. for 3, 6, 9 or 12 d are presented in Table 17. PPC on groups of carcasses significantly increased after three days of storage at 3° C. and every day thereafter throughout the storage period.

PPC correlated well to day of storage and odor production, indicating that it is acceptable for predicting the potential shelf-life of fresh chicken. However, the assay required a seven-day incubation period at 10° C., thereby making it unacceptable for practical use.

Total *P. fluorescens* (PFPC)±SEM for broiler chicken carcasses analyzed immediately (Day 0), or sampled after holding at 3° C. for 3, 6, 9 or 12 d are presented in Table 18. PFPC on groups of carcasses also significantly increased after three days of storage at 3° C. and every day thereafter throughout the storage period.

PFPC had higher $R^2$ values than PPC when correlated to day of storage and odor production, indicating that it would be a more precise method for predicting potential shelf-life of fresh chicken than PPC. However, PFPC estimations required 48 hours to conduct, thereby limiting its use as a practical method.

*P. fluorescens* impedance detection times (PDT)±SEM for broiler chicken carcasses analyzed immediately (Day 0), or sampled after holding at 3° C. for 3, 6, 9 or 12 d are presented in Table 19. PDT on groups of carcasses significantly decreased (indicating an increasing number of bacteria) from Day 0 to Day 12 during storage at 3° C.

$Log_{10}$ *P. fluorescens* impedance detection times (LPDT) using medium containing PSA were highly correlated to day of storage and odor production. Overall, LPDT estimations only required 1 to 26 h to conduct. LPDT using PSA in a suitable growth medium such as BHI would be the most practical method for predicting the potential shelf-life of fresh chicken. LPDT was also highly correlated to PPC and PFPC. LPDT determinations are an excellent means of estimating the total number of psychrotrophs and *P. fluorescens* on fresh broiler chicken carcasses and other fresh foods of animal origin.

Odor evaluation for broiler chicken carcasses analyzed immediately (Day 0), or sampled after holding at 3° C. for 3, 6, 9 or 12 d are presented in Table 20. Odor development on groups of carcasses significantly increased after three days of storage at 3° C. and every day thereafter throughout the storage period.

Linear and quadratic relationships and correlation coefficients for broiler chicken carcasses sampled immediately after processing (Day 0), or sampled after holding at 3° C. for 3, 6, 9 or 12 d and analyzed using total psychrotrophic plate counts (PPC), total *Pseudomonas fluorescens* counts (PFPC), $log_{10}$ *Pseudomonas fluorescens* capacitance detection times (LPDT), and odor evaluations are presented in Table 21. Significant linear and quadratic correlations, respectively, were observed between PPC and day of storage ($R^2$=0.86 and 0.84), PFPC and day of storage ($R^2$=0.85 and 0.89), LPDT and day of storage ($R^2$=0.86 and 0.85), odor production and day of storage ($R^2$=0.73 and 0.86), PPC and odor production ($R^2$=0.80 and 0.72), PFPC and odor production ($R^2$=0.87 and 0.81), LPDT and odor production ($R^2$=0.85 and 0.77), and LPDT and PPC ($R^2$=0.96 and 0.97). A significant linear correlation was observed between LPDT and PFPC ($R^2$=0.93). Hence, LPDT determinations that can be conducted in less than 24 hours can be used to precisely predict day of storage, odor production, PPC and PFPC.

Mead and Adams (1977) *Br. Poultry Sci.* 18: 661–670, observed that "the rapid isolation of psychrotrophic spoilage bacteria is of interest in relation to various foods and numerous attempts have been made previously to develop selective media which would permit more rapid growth of the organisms at higher incubation temperatures whilst inhibiting the growth of mesophiles." The results provided by the present disclosure indicate that *P. fluorescens* can be enumerated at the optimum growth temperature of 25° C. within 1 to 26 hours from broiler carcasses containing mixed populations of mesophilic and psychrotrophic bacteria using the methods and selective media described herein.

Enumeration of *P. fluorescens* from fresh poultry as described herein at day of processing benefits the poultry industry, and similar selective media and methods benefit the meat, fish and dairy industries in that the potential shelf-life of fresh chicken or other foods of animal origin is determined; processing sanitation hygiene is accurately determined; and temperature abuse subsequent to processing and/or distribution can be identified. For example, a product with an aerobic plate count (APC) of $10^4$ may have the same shelf life as a carcass with an APC of $10^2$ because the mesophilic bacteria enumerated at 35° C. using an APC are not responsible for spoiling refrigerated foods. However, this study indicates that a product with a significantly higher number of *P. fluorescens* will not last as long as one that has fewer spoilage bacteria, specifically *P. fluorescens*, at day of processing. Therefore, if on a given processing date, the number of *P. fluorescens* is significantly higher than usual, a failure in processing hygiene is presumed to have occurred, and the deleterious effect on product shelf-life is predictable. This sanitation break can be corrected that day (or the next) rather than having to wait the full 7 d required for completion of a PPC. Also, if a given group of carcasses or lot of other type of product is predicted to have a shelf-life of 12 d and lasts only 7 d, one concludes that the product has been exposed to temperature abuse. Using the method and *P. fluorescens*-selective media described herein, processors can identify and correct temperature abuse situations that arise during distribution and storage.

*P. fluorescens* is the most predominant of the three primary spoilage bacteria commonly associated with poultry, beef, pork, fish, shellfish and milk [Bishop and White (1985) *J. Food Prot.* 47:471–475; Fitz-Gerald and Deeth (1983) *Austral. J. Dairy Technol.* 38:97–103; Frieden, C. (1971) *Ann. Rev. Biochem.* 40:653–660; Hankin and Dillman (1968) *J. Milk Food Technol.* 31:141–145; Lockhead and Landerkin (1935) *Sci. Agr.* 15:765–770; Mead and Adams (1977) *Br. Poultry Sci.* 18: 661–670; Pooni and Mead (1984) *Food Microbiol.* 1:67–78; Russell et al. (1995) *Poultry Sci.* (In press); White and Little (1983) *J. Dairy Sci.* 66:268 (Abstr.); Wood and Baird (1943) *J. Fisheries Res. Board* 6:194–201]. Only chicken was evaluated in this study; however, because chicken has the most diverse microflora of the animal derived foods, this method can be used to predict the potential shelf-life of other fresh foods of animal origin besides chicken, including other poultry including, without limitation, duck, goose, dove, turkey, pheasant and quail; meats including, but not limited to, beef, veal, pork, lamb, beefalo, buffalo, kangaroo, ostrich and alligators; fresh water and salt water shellfish, and creams and milks of various origins.

EXAMPLES

Example 1

Development of a Selective Medium for *Pseudomonas fluorescens*

Ten whole ready-to-cook broiler chicken carcasses were obtained from the chiller exit of a commercial poultry processing plant. The carcasses were placed on ice, transported to the laboratory, individually bagged in sterile polyethylene bags (3000 cc $O_2$ at 22.8° C./$m^2$/24 hr at 1 atm), and maintained at 3° C. within 1 h of collection. The carcasses were sampled on the day of collection by rinsing in 100 mL of sterile deionized water according to the procedure described in Cox et al. (1981) *Poultry Sci.* 60:768–770.

Microbial Testing Using Brain Heart Infusion Broth with Irgasan

A stock solution was made by dissolving 2.5 g of 2, 4, 4'-trichloro-2'hydroxydiphenyl ether (Irgasan DP300, GAS#33-80345, Ciba-Geigy, Greensboro, N.C.) in 100 mL of 100% ethanol. An aliquot of the stock solution (0.1 mL) was then added to 100 mL of brain heart infusion broth (BHI, Difco Laboratories, Detroit, Mich.) to achieve a final concentration of 25 µg Irgasan/mL in the BHI-Irgasan (BHI-I) medium.

One milliliter of rinse fluid from each carcass was placed into 9 mL of BHI-I. Samples (1 mL) were assayed in duplicate in Bactometer module wells. Capacitance assays were conducted at 25° C. using test code 6 on the Bactometer Microbial Monitoring System M128 (bioMérieux Vitek, Inc., Hazelwood, Mo.). As soon as capacitance detection times (DT) were recorded, 1 ml. of the sample was immediately taken from the module well, placed into 9 mL of sterile Bacto-peptone (Difco Laboratories, Detroit, Mich.), diluted to $10^{-6}$, $10^{-7}$, or $10^{-8}$, spread onto duplicate plate count agar (PCA, Difco Laboratories, Detroit, Mich.) plates, and incubated at 25° C. for 48 h. Samples were diluted and plated because studies have shown that bacterial density must reach $10^6$ cells/mL or greater before changes in impedance, conductance, or capacitance of the medium are sufficient to be detected by the monitoring device [Firstenberg-Eden, R. (1983) *Food Technol* 37:64–70]. By culturing the sample immediately after detection, the bacterial species found on the plate at the highest dilution are assumed to be those responsible for changing the capacitance of the medium [Russell et al. (1995) *Food Protection* 58:1124–1128]. Plates from the highest dilution with 4 or more colonies per plate were used as the source of colonies for species identification. Four colonies per carcass were randomly selected, restreaked for isolation and purity on PCA, and incubated at 25° C. for 48 h (Table 1).

Bacterial isolates were analyzed for Gram reaction, catalase and cytochrome oxidase activity. The bacteria isolates were subsequently identified using the Nonfermentor card (NFC) with the Vitek AutoMicrobic System and API NFT strips (bioMérieux Vitek, Inc., Hazelwood, Mo.).

Seven species of bacteria from fresh broiler chicken carcasses were able to reach the threshold level of $10^6$ cells/mL in BHI-I and thereby change the capacitance of the medium sufficiently so as to be detected by the Bactometer. Because many of these species are not responsible for spoilage defects associated with fresh broilers, three basal media and BHI-I containing various antimicrobial compounds were analyzed to determine which combination could be used to allow only *Pseudomonas fluorescens* to reach the threshold level while suppressing the growth of the other bacterial species listed in Table 1.

Testing of Other Basal Media

Pseudomonas isolation agar (PIA, Difco Laboratories, Detroit, Mich.) is commonly used to select for *Pseudomonas* spp. in plate counts. Pseudomonas isolation medium without agar (PIM-AGAR) was prepared using the following ingredients per liter of deionized water: Bacto-peptone, 20 g (Difco Laboratories, Detroit, Mich.); Magnesium chloride, 1.4 g (Sigma Chemical Company, St. Louis, Mo.); Potassium sulfate, 10 g (Sigma Chemical Co.) Irgasan, 10,000 µg (Irgasan DP300, CAS#33-80345, Ciba-Geigy, Greensboro, N.C.). Five milliliters of PIM-AGAR were placed into sterile test tubes. Tubes of PIM-AGAR were each inoculated with one loopful (10 µl) of actively growing cultures of each of the bacterial isolates listed in Table 1. These tubes were incubated at 25° C. for 48 h. Visible turbidity was used to assess microbial growth. If turbidity was observed, the sample was scored positive for growth and if no turbidity was observed, the sample was scored negative for growth. If turbidity was slight, the sample was reported as positive/negative. Three replicate trials were conducted (Table 2).

Trimethylamine N-oxide (TMAO) medium was used because Easter et al. (1982) *J. Appl. Bacteriol.* 52:357–365 indicated that it was superior for enhancing impedance readings in samples containing spoilage bacteria, such as the pseudomonads. TMAO medium consisted of the following ingredients per liter of deionized water: Bacto-peptone, 5 g (Difco Laboratories, Detroit, Mich.); D-glucose, 2.5 g (Sigma Chemical Company, St. Louis, Mo.); NaCl, 20 g (J.T. Baker Chemical Company, Phillipsburg, N.J.); $K_2HPO_4$, 1 g (J.T. Baker Chemical Company, Phillipsburg, N.J.); $MgSO_4$, 1 g (J. T. Baker Chemical Company, Phillipsburg, N.J.); $NH_4Cl$, 0.5 g (J.T. Baker Chemical Co.) TMAO, 1 g (Aldrich Chemical Company, St. Louis, Mo.). Five milliliter aliquots of TMAO medium were placed in sterile test tubes. Tubes of TMAO medium were inoculated with each of the bacterial isolates listed in Table 1. These tubes were incubated at 25° C. for 48 h. Visible turbidity was used to assess microbial growth. If turbidity was observed, the sample was scored positive for growth and if no turbidity was observed, the sample was scored negative for growth. If turbidity was slight, the sample was reported as positive/negative. Three replicate trials were conducted.

General purpose medium plus (GPMP, bioMérieux Vitek, Inc., Hazelwood, Mo.) was also investigated as a basal medium with the addition of various antibiotics and chemicals (Table 6). GPMP is commonly used for conducting impedance determinations because it enhances the electrical changes produced by metabolizing bacteria. Three replicate tubes of each medium combination were each inoculated with one loopful (10 µl) of actively growing cultures of each bacterial isolate listed in Table 1.

Additives Used to Select for the Growth of *Pseudomonas fluorescens*

BHI was used as the basal medium because it is readily available and commonly used, PIM-AGAR and TMAO medium did not enhance the growth of *P. fluorescens* over the other bacterial isolates listed in Table 1 more efficiently than BHI (Tables 2 and 6, respectively), and GPMP did not produce acceptable impedance readings. To increase the selective capacity of BHI-I, antibiotics that inhibit *Aeromonas salmonicida salmonicida*, *Aeromonas sobria*, *Aeromonas hydrophila caviae*, *ribrio alginolyticus*, and *Serratia liquefaciens*, but allow the growth of *P. fluorescens* [Lorian, V. (1980) *Antibiotics in Laboratory Medicine* Williams and Wilkins, Baltimore, Md., London, U.K., 623–687] were used. Combinations of BHI-I and the following antibiotics and chemicals were used (Tables 3 through 9): ampicillin (Sigma Chemical Company, St. Louis, Mo.), carbenicillin (Sigma Chemical Company, St. Louis, Mo.), cephalothin (Sigma Chemical Company, St. Louis, Mo.), chloramphenicol (Sigma Chemical Company, St. Louis, Mo.), nitrofurantoin (Sigma Chemical Company, St. Louis, Mo.), NaCl (J.T. Baker Chemical Company, Phillipsburg, N.J.), and TMAO (Aldrich Chemical Company, St. Louis, Mo.).

To prepare each medium, brain heart infusion broth was mixed with deionized water, sterilized, and tempered to 25° C. Stock solutions of ampicillin, carbenicillin, cephalothin, and nitrofurantoin were prepared by dissolving 0.5 g, 0.4 g, 0.7 g and 0.001 g, respectively, into separate 10 mL tubes of deionized water to achieve final concentrations of 50,000, 40,000, 70,000 and 100 µg/mL respectively. Stock solutions of chloramphenicol and Irgasan were prepared by dissolving 0.1 g and 0.25 g, respectively, into separate 10 mL aliquots of 100% ethanol to achieve final concentrations of 10,000 and 25,000 µg/mL, respectively. A stock solution of TMAO was prepared by dissolving 10 g of TMAO in 100 mL deionized water to achieve a final concentration of 100,000 µg/mL. For media containing NaCl, NaCl was added directly to BHI before sterilization. All stock solutions containing antibiotics, Irgasan, and TMAO were filter sterilized using 0.2µ filters (Supor® Acrodisc® 25 syringe filter, Gelman Sciences, Ann Arbor, Mich.).

To determine the ability of the bacteria isolated in Table 1 to proliferate in BHI-I containing the various basal media, antibiotics, and chemicals, one loopful (10 µL) of each isolate at a concentration of over $10^6$ viable cells per ml was placed in triplicate into sterile clear polystyrene test tubes containing 5 milliliters of BHI-I or GPMP containing antibiotics and chemicals at concentrations listed in Tables 3 through 10. Tubes were incubated under aerobic conditions at 25° C. for 48 h. After incubation, each tube was placed into a colorimeter, and the percent transmittance was determined. Because media were different with regard to baseline transmittance, + and – symbols were also reported, such that +=bacteria produced visible turbidity in medium, ±=bacteria produced slight turbidity, and –=bacteria produced no visible turbidity (Tables 3 through 9). For Tables 1 through 8, 3 replicate trials were conducted and for Table 9, 5 replicate trials were conducted.

Once a medium (Table 10) was identified that allowed for the growth of *P. fluorescens* while suppressing the growth of the other bacteria isolated in Table 1, its usefulness for enumeration of *P. fluorescens* using capacitance was determined.

Example 2

Estimation of *P. fluorescens* Cell Numbers by Capacitance Measurement

Sample collection and Preparation

Twelve whole ready-to-cook broiler chicken carcasses were obtained from the chiller exit of a commercial broiler processing plant. The carcasses were placed on ice, transported to the laboratory, individually bagged in sterile polyethylene bags, and maintained at 3° C. within 1 h of collection. Two carcasses were sampled on the day of collection (Day 0). The remaining ten carcasses were refrigerated at 3° C., and 2 carcasses each were sampled after holding for each of the following times: 3, 6, 9, 12 and 15 d. Carcasses were sampled by rinsing in 100 mL of sterile deionized water according to the procedure described by Cox et al. (1981) *Poultry Sci.* 60:768–770. Three replicate trials were conducted.

The combination of ingredients added to BHI that was used to enumerate *P. fluorescens* was named *Pseudonomas fluorescens* selective additive (PSA). BHI-PSA contained the following ingredients per liter of sterile deionized water: brain heart infusion broth (37 g), nitrofurantoin (4 mg), carbenicillin (120 mg) and Irgasan (25 mg).

Wash fluid (1 mL) from each carcass was placed into 9 mL of brain heart infusion+*Pseudomonas fluorescens* selective additive (BHI+PSA). Samples (1 mL) were assayed in duplicate in the Bactometer Microbial Monitoring System M128 (bioMédrieux Vitek, Inc., Hazelwood, Mo.) using Test Code 6. As soon as capacitance detection times (DT) were recorded, 1 mL of the sample was immediately taken from the module well, placed into 9 mL of sterile Bactopeptone (Difco Laboratories, Detroit, Mich.), diluted to $10^{-6}$, $10^{-7}$, or $10^{-8}$, spread onto duplicate plate count agar (PCA, Difco Laboratories, Detroit, Mich.) plates, and incubated at 25° C. for 48 h according to the procedure described by Russell et al. [Russell et al. (1995) *Food Protection* 58:1124–1128]. Plates at the highest dilution with 4 or more colonies per plate were used for selection of bacterial isolates for identification. Four colonies per carcass were randomly selected, restreaked for isolation and purity on PCA, and incubated at 25° C. for 48 h (Tables 11 through 16).

Isolates chosen for identification were analyzed for Gram reaction, cytochrome oxidase and catalase activity. The bacterial isolates were subsequently identified using the Nonfermentor card (NFC) with the Vitek AutoMicrobic System and API NFT strips (bioMérieux Vitek, Inc., Hazelwood, Mo.).

In a second experiment, fifty whole ready-to-cook broiler chicken carcasses were obtained from the chiller exit of a commercial broiler processing facility in each of three replicate trials. The carcasses were transported to the laboratory on ice and individually bagged in sterile polyethylene bags (3000 cc $O_2$ at 22.8° C. per m$^2$ per 24 h at 1 atm). The carcasses were separated into five groups (ten carcasses each). The first ten carcasses were sampled at Day 0. Ten carcasses each were sampled after holding for 3, 6, 9 or 12 d at 3° C. Carcasses were sampled by rinsing with 100 mL of sterile deionized water according to the procedure described by Cox et al. (1981) *Poultry Sci.* 60:768–770.

Psychrotrophic plate counts were conducted on each carcass rinse according to the procedure described by Cousin et al. (1992) in: Compendium of Methods for the Microbiological Examination of Foods. C. Vanderzant and D. F. Splittstoesser, ed. American Public Health Association, Washington, D.C., p. 156–157, except that Petrifilm™ Aerobic Count Plates were used instead of total plate count agar. *Pseudomonas fluorescens* plate counts (PFPC) were determined using brain heart infusion agar with *Pseudomonas fluorescens* selective additive (BHI-PSA-AGAR) containing the following ingredients per mL of sterile deionized water: brain heart infusion broth 37 mg (BHI, Difco Laboratories, Detroit, Mich.); nitrofurantoin, 4 µg (Sigma Chemical Company, St. Louis, Mo.); carbenicillin, 120 µg (Sigma Chemical Company, St. Louis, Mo.); agar, 0.015 g (Sigma Chemical Company, St. Louis, Mo.); and Irgasan, 25 µg (Irgasan DP300, CAS#33-80345 Ciba-Geigy, Greensboro, N.C.). Plates were incubated at 25° C. for 48 h before colonies were counted.

One milliliter of rinse fluid from each carcass was placed into 9 mL of BHI-PSA and incubated until a detectable signal occurred in the capacitance measurement. Capacitance assays were conducted using test code 6 at 25° C. Samples (1 mL) were assayed in duplicate using the Bactometer Microbial Monitoring System M128 (bioMérieux Vitek, Inc., Hazelwood, Mo.).

Subjective odor evaluations were conducted by a trained 3-member panel. Carcasses at each sampling day were assigned a score of 1 to 5 with acceptable, perceptible odor, questionable, unacceptable, extremely unacceptable smelling carcasses receiving scores of 1, 2, 3, 4, and 5, respectively.

The experimental design was a 3×5×10 of replication, day, and carcass using a total of 150 carcasses. The data were converted to log values prior to statistical analysis. All microbiological analyses were conducted in duplicate on each carcass and the data were analyzed after averaging the duplicates. Results were analyzed using the General Linear Models (GLM) procedure of SAS® software [SAS Institute (1988) *SAS®/STAT Guide for Personal Computers*. Version 6.03 Edition. SAS Institute Inc. Cary, N.C.]. Upon testing day, replication, and day by replication interaction, were significant (P<0.05). Therefore, day by replication interaction was used as the error term. All values reported as significant were analyzed at the $\alpha=0.05$ level.

The preceding examples and disclosure are meant to illustrate the invention without limitation thereof. The skilled artisan may make obvious variations in medium nutrient components, incubation time or temperature or in the means by which microbial growth is detected, according to what is well known to the art.

TABLE 1

Number of isolates recovered from broiler chicken carcasses obtained from the chiller exit of a commercial processing plant and analyzed at Day 0 using brain heart infusion broth with 25 µg Irgasan/mL as the culture medium.

| Bacterial Species | Number [1,2] |
| --- | --- |
| Pseudomonas fluorescens | 14 |
| Pseudomonas putida | 4 |
| Aeromonas sobria | 2 |
| Aeromonas salmonicida salmonicida | 4 |
| Aeromonas hydrophila caviae | 2 |
| Vibrio alginolyticus | 2 |
| Serratia liquefaciens | 2 |

[1] Number of times a bacterial species was isolated from broiler carcasses.
[2] Six of the 36 bacterial isolates did not survive to be identified.

TABLE 2

Growth[1] of bacteria isolated using brain heart infusion broth with 25 µg Irgasan/mL in pseudomonas isolation medium[2] without agar.

| Bacterial isolate | Replicate | | |
| --- | --- | --- | --- |
|  | 1 | 2 | 3 |
| Pseudomonas fluorescens | + | + | + |
| Pseudomonas putida | + | + | + |
| Aeromonas sobria | + | + | + |
| Aeromonas salmonicida sal. | − | + | + |
| Aeromonas hydrophila caviae | + | + | + |
| Vibrio alginolyticus | + | + | + |
| Serratia liquefaciens | + | + | + |

[1] + = bacteria produced visible turbidity in medium, ± = bacteria produced slight turbidity, − = bacteria produced no visible turbidity at 450 nm.
[2] Pseudomonas isolation medium without agar (PIM-AGAR) consisted of the following ingredients per liter of deionized water: Bacto-peptone (20 g), Magnesium chloride (1.4 g), Potassium sulfate (10 g), and Irgasan (10 mg).

TABLE 3

Growth[1] of bacteria isolated (using brain heart infusion broth with 25 µg Irgasan/mL) in brain heart infusion broth with various levels of Irgasan, chloramphenicol, cephalothin, carbenicillin, NaCl, and trimethylamine N-oxide (TMAO) and TMAO medium[3].

| Bacterial isolate | Medium[2,3,4] | | | | | | | |
| --- | --- | --- | --- | --- | --- | --- | --- | --- |
|  | 1 | 2 | 3 | 4 | 5 | 6 | 7 | 8 |
| Pseudomonas fluorescens | 40− | 41− | 42− | 11+ | 10+ | 20+ | 14+ | 22+ |
| Pseudomonas putida | 35− | 43− | 42− | 38− | 15+ | 39− | 25+ | 22+ |
| Aeromonas sobria | 30+ | 34− | 37− | 19+ | 8+ | 36− | 10+ | 21+ |
| Aeromonas salmonicida sal. | 24± | 31± | 33± | 38− | 16+ | 40− | 9+ | 18+ |
| Aeromonas hydrophila cav. | 25± | 31± | 35± | 37− | 22+ | 39− | 9+ | 20+ |
| Vibrio alginolyticus | 33± | 35± | 41− | 40− | 15+ | 40− | 10+ | 22+ |
| Serratia liquefaciens | 29± | 30± | 34± | 37− | 16+ | 41− | 9+ | 21+ |
| Control[5] | 47 | 47 | 46 | 47 | 46 | 46 | 45 | 75 |

[1] Growth was determined using a colorimeter with a 450 nm filter. Results are reported as % transmittance. Because media were different with regard to baseline transmittance, + and − symbols are also reported: +, bacteria produced visible turbidity in medium, ±, bacteria produced slight turbidity, −, bacteria produced no visible turbidity.
[2] Media 1–7 consisted of BHI broth with the following additives per mL: 1) Irgasan (25 µg), chloramphenicol (10 µg); 2) Irgasan (25 µg), chloramphenicol (20 µg); 3) Irgasan (25 µg), chloramphenicol (30 µg); 4) cephalothin (700 µg), carbenicillin (400 µg); 5) cephalothin (700 µg); 6) cephalothin (700 µg), carbenicillin (400 µg), NaCl (15 mg), TMAO (1 mg); 7) Irgasan (25 µg).
[3] Medium 8 (TMAO medium) consisted of the following ingredients per 100 mL of deionized water: Bacto-peptone (.5 g), D-glucose (.25 g), NaCl (2 g), $K_2HPO_4$ (.1 g), $MgSO_4$ (.1 g), $NH_4Cl$ (.05 g), and TMAO (.1 g).
[4] n = 3.
[5] Control = baseline colorimetric values for the medium without inoculum.

TABLE 4

Growth[1] of bacteria (isolated using brain heart infusion broth with 25 µg Irgasan/mL) in brain heart infusion broth with various levels of Irgasan, ampicillin, cephalothin, carbenicillin, NaCl, and trimethylamine N-oxide (TMAO).

| Bacterial isolate | Medium[2,3] | | | | | | | |
| --- | --- | --- | --- | --- | --- | --- | --- | --- |
|  | 1 | 2 | 3 | 4 | 5 | 6 | 7 | 8 |
| Pseudomonas fluorescens | 12+ | 12+ | 12+ | 12+ | 14+ | 15+ | 13+ | 13+ |
| Pseudomonas putida | 25+ | 33± | 34± | 35± | 37± | 38− | 40− | 40− |
| Aeromonas sobria | 7+ | 10+ | 8+ | 8+ | 10+ | 7+ | 17+ | 19+ |
| Aeromonas salmonicida sal. | 15+ | 23+ | 32± | 43− | 41− | 42− | 38− | 40− |
| Aeromonas hydrophila cav. | 22+ | 23+ | 27± | 41− | 46− | 43− | 42− | 42− |
| Vibrio alginolyticus | 23+ | 32± | 34± | 36± | 43− | 43− | 39− | 41− |
| Serratia liquefaciens | 13+ | 22+ | 32± | 41− | 45− | 43− | 41− | 42− |
| Control[4] | 42 | 43 | 45 | 47 | 48 | 49 | 49 | 49 |

[1] Growth was determined using a colorimeter with a 450 nm filter. Results are reported as % transmittance. Because media were different with regard to baseline transmittance, + and − symbols are also reported, where + = bacteria produced visible turbidity in medium, ± = bacteria produced slight turbidity, − = bacteria produced no visible turbidity.

TABLE 4-continued

Growth[1] of bacteria (isolated using brain heart infusion broth with 25 μg Irgasan/mL) in brain heart infusion broth with various levels of Irgasan, ampicillin, cephalothin, carbenicillin, NaCl, and trimethylamine N-oxide (TMAO).

| Bacterial isolate | Medium[2,3] | | | | | | | |
|---|---|---|---|---|---|---|---|---|
| | 1 | 2 | 3 | 4 | 5 | 6 | 7 | 8 |

[2]Media 1–8 consisted of BHI broth with the following additives per mL: 1) ampicillin (50 μg); 2) ampicillin (75 μg); 3) ampicillin (100 μg); 4) carbenicillin (100 μg), ampicillin (10 μg); 5) carbenicillin (100 μg), cephalothin (100 μg), ampicillin (10 μg); 6) carbenicillin (200 μg), ampicillin (10 μg), NaCl (10 mg), trimethylamine N-oxide (TMAO-1 mg); 7) cephalothin (200 μg), carbenicillin (100 μg), NaCl (10 mg), TMAO (1 mg); 8) cephalothin (400 μg), carbenillin (300 μg), NaCl (10 mg), TMAO (1 mg).
[3]n = 3.
[4]Control = baseline colorimetric values for the medium without inoculum.

TABLE 5

Growth[1] of bacteria (isolated using brain heart infusion broth with 25 μg Irgasan/mL) in brain heart infusion broth with various levels of cephalothin, carbenicillin, NaCl, and trimethyamine N-oxide (TMAO).

| Bacterial isolate | Medium[2,3] | | | | | |
|---|---|---|---|---|---|---|
| | 1 | 2 | 3 | 4 | 5 | 6 |
| Pseudomonas fluorescens | 13+ | 18+ | 25+ | 16+ | 15+ | 29+ |
| Pseudomonas putida | 29+ | 42– | 44– | 43– | 44– | 43– |
| Aeromonas sobria | 10+ | 12+ | 13+ | 42– | 42– | 43– |
| Aeromonas salmonicida sal. | 42– | 43– | 44– | 43– | 43– | 42– |
| Aeromonas hydrophila cav. | 42– | 41– | 43– | 43– | 42– | 43– |
| Vibrio alginolyticus | 40– | 44– | 46– | 43– | 43– | 43– |
| Serratia liquefaciens | 41– | 42– | 44– | 44– | 43– | 43– |
| Control[4] | 47 | 50 | 52 | 51 | 51 | 50 |

[1]Growth was determined using a colorimeter with a 450 nm filter. Results are reported as % transmittance. Because media were different with regard to baseline transmittance, + and – symbols are also reported, where + = bacteria produced visible turbidity in medium, ± = bacteria produced slight turbidity, – = bacteria produced no visible turbidity.
[2]Media 1-6 consisted of BHI broth with the following additives per mL: 1) carbenicillin (200 μg); 2) carbenicillin (400 μg); 3) carbenicillin (600 μg); 4) cephalothin (500 μg), carbenicillin (300 μg), NaCl (10 mg), TMAO (1 mg); 5) cephalothin (1000 μg), carbenicillin (300 μg), NaCl (10 mg), TMAO (1 mg); 6) cephalothin (500 μg), carbenicillin (600 μg), NaCl (10 mg), TMAO (1 mg).
[3]n = 3.
[4]Control = baseline colorimetric values for the medium without inoculum.

TABLE 6

Growth[1] of bacteria (isolated using brain heart infusion broth with 25 μg Irgasan/mL) in brain heart infusion broth with various levels of cephalothin, carbenicillin, NaCl, and trimethyamine N-oxide (TMAO).

| Bacterial isolate | Medium[2,3] | | | | | |
|---|---|---|---|---|---|---|
| | 1 | 2 | 3 | 4 | 5 | 6 |
| Pseudomonas fluorescens | 53± | 58– | 60– | 45+ | 38+ | 57– |
| Pseudomonas putida | 51+ | 61– | 62– | 56– | 61– | 58– |
| Aeromonas sobria | 12+ | 13+ | 13+ | 61– | 65– | 62– |
| Aeromonas salmonicida sal. | 59– | 60– | 61– | 58– | 62– | 58– |
| Aeromonas hydrophila cav. | 54± | 56± | 56± | 55± | 60– | 60– |
| Vibrio alginolyticus | 60– | 61– | 64– | 58– | 62– | 63– |
| Serratia liquefaciens | 55– | 58– | 62– | 57– | 62– | 62– |
| Control[4] | 70 | 68 | 68 | 66 | 67 | 68 |

[1]Growth was determined using a colorimeter with a 450 nm filter. Results are reported as % transmittance. Because media were different with regard to baseline transmittance, + and – symbols are also reported, where + = bacteria produced visible turbidity in medium, ± = bacteria produced slight turbidity, – = bacteria produced no visible turbidity.

TABLE 6-continued

Growth[1] of bacteria (isolated using brain heart infusion broth with 25 μg Irgasan/mL) in brain heart infusion broth with various levels of cephalothin, carbenicillin, NaCl, and trimethyamine N-oxide (TMAO).

| Bacterial isolate | Medium[2,3] | | | | | |
|---|---|---|---|---|---|---|
| | 1 | 2 | 3 | 4 | 5 | 6 |

[2]Media 1–6 consisted of GPMP broth with the following additives per mL: 1) carbenicillin (200 μg); 2) carbenicillin (400 μg); 3) carbenicillin (600 μg); 4) cephalothin (500 μg), carbenicillin (300 μg), NaCl (10 mg), TMAO (1 mg); 5) cephalothin (1000 μg), carbenicillin (300 μg), NaCl (10 mg), TMAO (1 mg); 6) cephalothin (500 μg), carbenicillin (600 μg), NaCl (10 mg), TMAO (1 mg).
[3]n = 3.
[4]Control = baseline colorimetric values for the medium without inoculum.

TABLE 7

Growth[1] of bacteria (isolated using brain heart infusion broth with 25 μg Irgasan/mL) in brain heart infusion broth with various levels of nitrofurantoin, carbenicillin, Irgasan and trimethylamine N-oxide (TMAO).

| Bacterial isolate | Medium[2,3] | | | | | | | |
|---|---|---|---|---|---|---|---|---|
| | 1 | 2 | 3 | 4 | 5 | 6 | 7 | 8 |
| Pseudomonas fluorescens | 17+ | 18+ | 17+ | 14+ | 20+ | 16+ | 15+ | 13+ |
| Pseudomonas putida | 21+ | 23+ | 20+ | 19± | 46– | 39– | 35– | 31– |
| Aeromonas sobria | 34– | 30– | 27– | 23– | 29± | 39– | 33– | 30– |
| Aeromonas salmonicida sal. | 34– | 31– | 27– | 23– | 45– | 39– | 34– | 31– |
| Aeromonas hydrophila cav. | 33– | 30– | 27– | 23– | 45– | 38– | 34– | 29– |
| Vibrio alginolyticus | 33– | 31– | 27– | 23– | 46– | 37– | 34– | 28– |
| Serratia liquefaciens | 32– | 31– | 27– | 23– | 46– | 36– | 35– | 29– |
| Control[4] | 36 | 32 | 28 | 24 | 49 | 43 | 37 | 34 |

[1]Growth was determined using a colorimeter with a 450 nm filter. Results are reported as % transmittance. Because media were different with regard to baseline transmittance, + and – symbols are also reported, where + = bacteria produced visible turbidity in medium, ± = bacteria produced slight turbidity, – = bacteria produced no visible turbidity. Nitrofurantoin level greatly affected % transmittance.
[2]Media 1–8 consisted of BHI broth with the following additives per mL: 1) nitrofurantoin (50 μg), carbenicillin (80 μg); 2) nitrofurantoin (75 μg), carbenicillin (80 μg); 3) nitrofurantoin (100 μg), carbenicillin (80 μg); 4) nitrofurantoin (150 μg), carbenicillin (80 μg); 5) carbenicillin (80 μg), Irgasan (25 μg); 6) nitrofurantoin (25 μg), carbenicillin (80 μg), Irgasan (25 μg), TMAO (1 mg); 7) nitrofurantoin (50 μg), carbenicillin (80 μg), Irgasan (25 μg), TMAO (1 mg); 8) nitrofurantoin (75 μg), carbenicillin (80 μg), Irgasan (25 μg), TMAO (1 mg).
[3]n = 3.
[4]Control = baseline colorimetric values for the medium without inoculum.

TABLE 8

Growth[1] of bacteria (isolated using brain heart infusion broth with 25 μg Irgasan/mL) in brain heart infusion broth with various levels of nitrofurantoin, carbenicillin, Irgasan and trimethylamine N-oxide (TMAO).

| Bacterial isolate | Medium[2,3] | | | | | | | |
|---|---|---|---|---|---|---|---|---|
| | 1 | 2 | 3 | 4 | 5 | 6 | 7 | 8 |
| Pseudomonas fluorescens | 25+ | 21+ | 22+ | 21+ | 19+ | 21+ | 24+ | 19+ |

TABLE 8-continued

Growth[1] of bacteria (isolated using brain heart infusion broth with 25 μg Irgasan/mL) in brain heart infusion broth with various levels of nitrofurantoin, carbenicillin, Irgasan and trimethylamine N-oxide (TMAO).

| Bacterial isolate | Medium[2,3] | | | | | | | |
|---|---|---|---|---|---|---|---|---|
| | 1 | 2 | 3 | 4 | 5 | 6 | 7 | 8 |
| Pseudomonas putida | 41– | 41– | 44– | 44– | 41– | 42– | 39– | 38– |
| Aeromonas sobria | 42– | 39– | 38– | 8+ | 12+ | 10+ | 12+ | 8+ |
| Aeromonas salmonicida sal. | 43– | 42– | 42– | 43– | 38– | 32± | 30± | 19+ |
| Aeromonas hydrophila cav. | 21+ | 16+ | 19+ | 34± | 35± | 34± | 33± | 21+ |
| Vibrio alginolyticus | 30± | 19+ | 15+ | 10+ | 15+ | 33± | 20+ | 32± |
| Serratia liquefaciens | 40– | 42– | 41– | 42– | 36± | 37± | 35± | 33± |
| Control[4] | 43 | 43 | 44 | 46 | 46 | 46 | 46 | 47 |

[1]Growth was determined using a colorimeter with a 450 nm filter. Results are reported as % transmittance. Because media were different with regard to baseline transmittance, + and – symbols are also reported, where + = bacteria produced visible turbidity in medium, ± = bacteria produced slight turbidity, – = bacteria produced no visible turbidity. Nitrofurantoin level greatly affected % transmittance.
[2]Media 1–8 consisted of BHI broth with the following additives per mL: 1) nitrofurantoin (20 μg), carbenicillin (300 μg), Irgasan (20 μg), TMAO (1 mg); 2) nitrofurantoin (15 μg), carbenicillin (250 μg), Irgasan (15 μg), TMAO (1 mg); 3) nitrofurantoin (10 μg), carbenicillin (200 μg) Irgasan (10 μg), TMAO (1 mg); 4) nitrofurantoin (5 μg), carbenicillin (150 μg), Irgasan (5 μg), TMAO (1 mg); 5) nitrofurantoin (4 μg), carbenicillin (120 μg), Irgasan (5 μg); 6) nitrofurantoin (3 μg), carbenicillin (80 μg), Irgasan (5 μg); 7) nitrofurantoin (2 μg), carbenicillin (40 μg), Irgasan (5 μg); 8) nitrofurantoin (1 μg), carbenicillin (20 μg), Irgasan (5 μg).
[3]n = 3.
[4]Control = baseline colorimetric values for the medium without inoculum.

TABLE 9

Growth[1] of bacteria (isolated using brain heart infusion broth with 25 μg Irgasan/mL) in brain heart infusion broth with nitrofurantoin, Irgasan, and various levels of carbenicillin.

| Bacterial isolate | Medium[2,3] | | | |
|---|---|---|---|---|
| | 1 | 2 | 3 | 4 |
| Pseudomonas fluorescens | 14+ | 16+ | 15+ | 16+ |
| Pseudomonas putida | 39– | 40– | 41– | 40– |
| Aeromonas sobria | 22+ | 17+ | 17+ | 18+ |
| Aeromonas salmonicida sal. | 40– | 39– | 38– | 37– |
| Aeromonas hydrophila cav. | 41– | 39– | 37– | 35– |
| Vibrio alginolyticus | 42– | 42– | 41– | 40– |
| Serratia liquefaciens | 41– | 39– | 39– | 36– |
| Control[4] | 44 | 44 | 43 | 43 |

[1]Growth was determined using a colorimeter with a 450 nm filter. Results are reported as % transmittance. Because media were different with regard to baseline transmittance, + and – symbols are also reported, where + = bacteria produced visible turbidity in medium, ± = bacteria produced slight turbidity, – = bacteria produced no visible turbidity. Nitrofurantoin level greatly affected % transmittance.
[2]Media 1–4 consisted of BHI broth with the following additives per mL: 1) nitrofurantoin (4 μg), carbenicillin (100 μg), Irgasan (25 μg); 2) nitrofurantoin (4 μg), carbenicillin (75 μg), Irgasan (25 μg); 3) nitrofurantoin (4 μg), carbenicillin (50 μg), Irgasan (25 μg); 4) nitrofurantoin (4 μg), carbenicillin (25 μg), Irgasan (25 μg).
[3]n = 3.
[4]Control = baseline colorimetric values for the medium without inoculum.

TABLE 10

Growth[1] of bacteria (isolated using brain heart infusion broth with 25 μg Irgasan/mL) in brain heart infusion broth with the following additives per mL of medium: nitrofurantoin (4 μg), carbenicillin (120 μg), Irgasan (25 μg).

| Bacterial isolate | Replicate | | | | |
|---|---|---|---|---|---|
| | 1 | 2 | 3 | 4 | 5 |
| Pseudomonas fluorescens | 36+ | 35+ | 42+ | 36+ | 36+ |
| Pseudomonas putida | 52– | 53– | 52– | 51– | 53– |
| Aeromonas sobria | 52– | 52– | 52– | 52– | 52– |
| Aeromonas salmonicida sal. | 52– | 53– | 53– | 52– | 53– |
| Aeromonas hydrophila cav. | 52– | 52– | 53– | 50– | 52– |
| Vibrio alginolyticus | 53– | 54– | 54– | 53– | 54– |
| Serratia liquefaciens | 52– | 52– | 51– | 52– | 53– |
| Control[4] | 60 | 60 | 60 | 60 | 60 |

[1]Growth was determined using a colorimeter with a 450 nm filter. Results are reported as % transmittance. Because media were different with regard to baseline transmittance, + and – symbols are also reported, where + = bacteria produced visible turbidity in medium, ± = bacteria produced slight turbidity, – = bacteria produced no visible turbidity. Nitrofurantoin level greatly affected % transmittance.
[2]Control = baseline colorimetric values for the medium without inoculum.

TABLE 11

Number of isolates recovered from broiler chicken carcasses obtained from the chiller exit of a commercial processing plant and analyzed at Day 0 using brain heart infusion broth with Pseudomonas fluorescens selective additive (BHI-PSA) as the culture medium.

| Bacterium | Day 0 | | | | | |
|---|---|---|---|---|---|---|
| | Rep 1 | | Rep 2 | | Rep 3 | |
| | Bird 1 | Bird 2 | Bird 1 | Bird 2 | Bird 1 | Bird 2 |
| Pseudomonas fluorescens | 1 | 0 | 2* | 2* | 2* | 1* |
| Pseudomonas putida | 3* | 4* | 2 | 2 | 2 | 2 |
| CDC EF-4 | 0 | 0 | 0 | 0 | 0 | 1 |

*Predominant bacterium visually observed on plates at the highest dilution.

TABLE 12

Number of isolates recovered from broiler chicken carcasses obtained from the chiller exit of a commercial processing plant and analyzed after 3 days of storage at 3° C. using brain heart infusion broth with Pseudomonas fluorescens selective additive (BHI-PSA) as the culture medium.

| Bacterium | Day 3 | | | | | |
|---|---|---|---|---|---|---|
| | Rep 1 | | Rep 2 | | Rep 3 | |
| | Bird 1 | Bird 2 | Bird 1 | Bird 2 | Bird 1 | Bird 2 |
| Pseudomonas fluorescens | 1 | 4* | 3* | 4* | 4* | 4* |
| Pseudomonas putida | 3* | 0 | 0 | 0 | 0 | 0 |
| Flavobacterium meningosepticum | 0 | 0 | 1 | 0 | 0 | 0 |

*Predominant bacterium visually observed on plates at the highest dilution.

TABLE 13

Number of isolates recovered from broiler chicken carcasses obtained from the chiller exit of a commercial processing plant and analyzed after 6 days of storage at 3° C. using brain heart infusion broth with *Pseudomonas fluorescens* selective additive (BHI-PSA) as the culture medium.

| | Day 6 | | | | | |
|---|---|---|---|---|---|---|
| | Rep 1 | | Rep 2 | | Rep 3 | |
| Bacterium | Bird 1 | Bird 2 | Bird 1 | Bird 2 | Bird 1 | Bird 2 |
| *Pseudomonas fluorescens* | 4* | 4* | 4* | 2* | 2* | 4* |
| *Pseudomonas putida* | 0 | 0 | 0 | 1 | 2 | 0 |
| *Flavobacterium meningosepticum* | 0 | 0 | 0 | 1 | 0 | 0 |

*Predominant bacterium visually observed on plates at the highest dilution.

TABLE 14

Number of isolates recovered from broiler chicken carcasses obtained from the chiller exit of a commercial processing plant and analyzed after 9 days of storage at 3° C. using brain heart infusion broth with *Pseudomonas fluorescens* selective additive (BHI-PSA) as the culture medium.

| | Day 9 | | | | | |
|---|---|---|---|---|---|---|
| | Rep 1 | | Rep 2 | | Rep 3 | |
| Bacterium | Bird 1 | Bird 2 | Bird 1 | Bird 2 | Bird 1 | Bird 2 |
| *Pseudomonas fluorescens* | 3* | 4* | 2* | 2* | 4* | 4* |
| *Pseudomonas putida* | 1 | 0 | 1 | 1 | 0 | 0 |
| *Aeromonas hydrophila caviae* | 0 | 0 | 1 | 0 | 0 | 0 |
| Gram negative bacillus | 0 | 0 | 0 | 1 | 0 | 0 |

*Predominant bacterium visually observed on plates at the highest dilution.

TABLE 15

Number of isolates recovered from broiler chicken carcasses obtained from the chiller exit of a commercial processing plant and analyzed after storage for 12 days at 3° C. using brain heart infusion broth with *Pseudomonas fluorescens* selective additive (BHI-PSA) as the culture medium.

| | Day 12 | | | | | |
|---|---|---|---|---|---|---|
| | Rep 1 | | Rep 2 | | Rep 3 | |
| Bacterium | Bird 1 | Bird 2 | Bird 1 | Bird 2 | Bird 1 | Bird 2 |
| *Pseudomonas fluorescens* | 2* | 4* | 4* | 4* | 2* | 1* |
| *Pseudomonas putida* | 1 | 0 | 0 | 0 | 2 | 0 |
| CDC-EF4 | 1 | 0 | 0 | 0 | 0 | 0 |
| Gram-negative bacillus | 0 | 0 | 0 | 0 | 0 | 2 |
| *Alcaligenes* spp. | 0 | 0 | 0 | 0 | 0 | 1 |

*Predominant bacterium visually observed on plates at the highest dilution.

TABLE 16

Number of isolates recovered from broiler chicken carcasses obtained from the chiller exit of a commercial processing plant and analyzed after storage for 15 days at 3° C. using brain heart infusion broth with *Pseudomonas fluorescens* selective additive (BHI-PSA) as the culture medium.

| | Day 15 | | | | | |
|---|---|---|---|---|---|---|
| | Rep 1 | | Rep 2 | | Rep 3 | |
| Bacterium | Bird 1 | Bird 2 | Bird 1 | Bird 2 | Bird 1 | Bird 2 |
| *Pseudomonas fluorescens* | 3* | 4* | 2* | 3* | 3* | 3* |
| *Pseudomonas putida* | 0 | 0 | 2 | 1 | 1 | 0 |
| *Chromobacterium violaceum* | 1 | 0 | 0 | 0 | 0 | 0 |
| CDC EF-4 | 0 | 0 | 0 | 0 | 0 | 1 |

*Predominant bacterium visually observed on plates at the highest dilution.

TABLE 17

Total psychrotrophic plate counts (PPC)[1] ± SEM for broiler chicken carcasses analyzed immediately (Day 0), or sampled after holding at 3° C. for 3, 6, 9 or 12 d.

| | PPC ($\log_{10}$ colony forming units (CFU)/mL) | | | |
|---|---|---|---|---|
| Day of Storage | Replicate 1 | Replicate 2 | Replicate 3 | Total |
| 0 | 3.31 ± .17 | 2.83 ± .17 | 3.47 ± .04 | 3.07 ± .13[d] |
| 3 | 2.63 ± .07 | 3.29 ± .13 | 3.83 ± .13 | 2.96 ± .11[d] |
| 6 | 4.84 ± .24 | 5.76 ± .29 | 7.77 ± .24 | 5.28 ± .21[c] |
| 9 | 7.42 ± .22 | 9.53 ± .05 | 7.90 ± .33 | 8.48 ± .26[b] |
| 12 | 9.99 ± .08 | 9.84 ± .05 | 10.12 ± .05 | 9.91 ± .05[a] |
| n | 10 | 10 | 10 | 30 |

[1]PPC were conducted using Pertifilm™ Aerobic Count Plates incubated at 10° C. for 7 d.
[a–e]Means within columns with no common superscript differ significantly ($P < 0.05$).

TABLE 18

Total *Pseudomonas fluorescens* (PFPC)[1] ± SEM for broiler chicken carcasses analyzed immediately (Day 0), or sampled after holding at 3° C. for 3, 6, 9 or 12 d.

| | PFPC ($\log_{10}$ colony forming units (CFU)/mL) | | | |
|---|---|---|---|---|
| Day of Storage | Replicate 1 | Replicate 2 | Replicate 3 | Total |
| 0 | 1.69 ± .16 | 0.90 ± .07 | 2.05 ± .04 | 1.29 ± .12[d] |
| 3 | 2.00 ± .09 | 2.22 ± .07 | 2.18 ± .10 | 2.11 ± .06[d] |
| 6 | 2.50 ± .19 | 2.66 ± .11 | 4.63 ± .23 | 2.59 ± .11[c] |
| 9 | 4.29 ± .12 | 5.76 ± .24 | 5.32 ± .27 | 5.02 ± .21[b] |
| 12 | 7.02 ± .13 | 7.27 ± .16 | 7.77 ± .08 | 7.14 ± .10[a] |
| n | 10 | 10 | 10 | 30 |

[1]PFPC were conducted using a medium containing the following ingredients per mL of sterile deionized water: brain heart infusion broth (37,000 μg), nitrofurantoin (4 μg), carbenicillin (120 μg), agar (.015 g), and Irgasan (25 μg) incubated at 25° C. for 48 h.
[a–e]Means within columns with no common superscript differ significantly ($P < 0.05$).

TABLE 19

*Pseudomonas fluorescens* impedance detection times (PDT)[1]
± SEM for broiler chicken carcasses analyzed immediately (Day 0),
or sampled after holding at 3° C. for 3, 6, 9 or 12 d.

| Day of Storage | PDT (hours) | | | |
|---|---|---|---|---|
| | Replicate 1 | Replicate 2 | Replicate 3 | Total |
| 0 | 23.79 ± 2.12 | 33.25 ± 2.60 | 19.98 ± .39 | 25.67 ± 1.50[a] |
| 3 | 17.20 ± .53 | 17.06 ± .61 | 15.26 ± .59 | 16.51 ± .36[b] |
| 6 | 12.00 ± .77 | 9.15 ± .85 | 4.18 ± .55 | 8.44 ± .73[c] |
| 9 | 4.11 ± .43 | 1.00 ± .00 | 3.54 ± .66 | 3.28 ± .29[d] |
| 12 | 1.00 ± .00 | 1.00 ± .00 | 1.00 ± .00 | 1.00 ± .00[e] |
| n | 10 | 10 | 10 | 30 |

[1]PDT were determined by monitoring capacitance in medium containing the following
ingredients per mL of sterile deionized water: brain heart infusion broth (37,000 μg), nitrofurantoin (4 μg), carbenicillin (120 μg), and Irgasan (25 μg) incubated at 25° C.
[a-e]Means within columns with no common superscript differ significantly (P < 0.05).

TABLE 20

Odor evaluation for broiler chicken carcasses analyzed
immediately (Day 0), or sampled after holding at 3° C.
for 3, 6, 9 or 12 d.

| Day of Storage | Odor[1] | | | |
|---|---|---|---|---|
| | Replicate 1 | Replicate 2 | Replicate 3 | Total |
| 0 | 1 | 1 | 1 | 1[d] |
| 3 | 1 | 1 | 1 | 1[d] |
| 6 | 1 | 1 | 2 | 1.33[c] |
| 9 | 1.9 | 4.2 | 2.7 | 2.93[b] |
| 12 | 4.8 | 5 | 5 | 4.93[a] |
| n | 10 | 10 | 10 | 30 |

[1]Odor was determined using a trained 3 member panel. Odor scores were as follows: 1 = fresh chicken, 2 = perceptable odor, 3 = questionable with regard to acceptability, 4 = unacceptable, 5 = extremely objectionable.
[a-e]Means within columns with no common superscript differ significantly (P < 0.05).

TABLE 21

Linear and quadratic correlation coefficients for
broiler chicken carcasses sampled immediately after
processing (Day 0), or sampled after holding at
3° C. for 3, 6, 9 or 12 d and analyzed using
total psychrotrophic plate counts (PPC)[1],
total *Pseudomonas fluorescens* counts (PFPC)[2],
log₁₀ *Pseudomonas fluorescens* impedance
detection times (PDT)[3], and odor evaluations[4].

| Comparison | Linear $R^2$ | $P < .05$ | Quadratic $R^2$ | $P < .05$ |
|---|---|---|---|---|
| PPC versus day of storage | .86 | .0001 | .84 | .0004 |
| PFPC versus day of storage | .85 | .0001 | .89 | .0001 |
| LPDT versus day of storage | .86 | .0001 | .85 | .0003 |
| Odor versus day of storage | .73 | .0001 | .86 | .0001 |
| PPC versus odor | .80 | .0001 | .72 | .0001 |
| PFPC versus odor | .87 | .0001 | .81 | .0001 |
| LPDT versus odor | .85 | .0001 | .77 | .0001 |
| LPDT versus PFPC | .93 | .0001 | .86 | .2339 |
| LPDT versus PPC | .96 | .0001 | .97 | .0020 |

[1]PPC were conducted using Petrifilm ™ Aerobic Count Plates incubated at 10° C. for 7 d.
[2]PFPC were conducted using a medium containing the following ingredients per mL of sterile deionized water: brain heart infusion broth (37,000 μg), nitrofurantoin (4 μg),

TABLE 21-continued

Linear and quadratic correlation coefficients for
broiler chicken carcasses sampled immediately after
processing (Day 0), or sampled after holding at
3° C. for 3, 6, 9 or 12 d and analyzed using
total psychrotrophic plate counts (PPC)[1],
total *Pseudomonas fluorescens* counts (PFPC)[2],
log₁₀ *Pseudomonas fluorescens* impedance
detection times (PDT)[3], and odor evaluations[4].

| Comparison | Linear $R^2$ | $P < .05$ | Quadratic $R^2$ | $P < .05$ |
|---|---|---|---|---| carbenicillin (120 μg), agar (.015 g), and Irgasan (25 μg) incubated at 25° C. for 48 h.
[3]PDT were determined by monitoring capacitance in medium containing the following
ingredients per mL of sterile deionized water: brain heart infusion broth (37,000 μg), nitrofurantoin (4 μg), carbenicillin (120 μg), and Irgasan (25 μg) incubated at 25° C.
[4]Odor was determined using a trained 3 member panel.

I claim:

1. A bacteriological growth medium selective for *Pseudomonas fluorescens*, said selective medium comprising a nutrient component capable of supporting growth of *P. fluorescens* and a compound of the formula

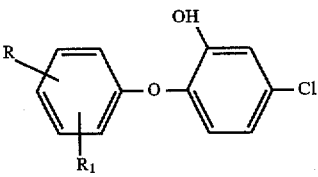

where R is a halogen and $R_1$ is H or Cl, at a concentration of between about 1 and 50 μg/mL, carbenicillin at a concentration of between 5 and 800 μg/ml and nitrofurantoin at a concentration of between about 1 and about 200 μg/mL.

2. The medium of claim 1 comprising Irgasan at a concentration of about 25 to about 30 μg/mL, carbenicillin at a concentration of about 120 to about 130 μg/mL and nitrofurantoin at a concentration of about 3 to about 20 μg/mL.

3. The medium of claim 2 comprising a compound of the formula Irgasan at a concentration of Irgasan of 25 μg/mL, carbenicillin at a concentration of 120 μg/mL and nitrofurantoin at a concentration of 4 μg/mL.

4. A method for the detection of *Pseudomonas fluorescens* in or on a fresh animal product, said method comprising the steps of:

a) washing a sample of said fresh animal product with a suitable sterile diluent to produce a product wash fluid;

b) inoculating the bacteriological growth medium of claim 2 with an aliquot of the wash fluid of step (a), said nutrient component of said bacteriological growth being suitable for impedance measurements, to produce inoculated selective growth medium;

c) incubating said inoculated selective growth medium at a temperature between about 10° and 30° C.;

d) detecting microbial growth by measuring decrease in impedance, increase in capacitance or increase in turbidity of the incubated growth medium of step (c) in comparison to uninoculated medium at intervals from about 1 to about 10 hours or until a detectable change in impedance, capacitance or turbidity in said incubated, inoculated, selective growth medium;

whereby *P. fluorescens* is detected in or on said fresh animal product when the impedance, capacitance or turbidity of the incubated, inoculated selective growth medium is detectably increased as compared to the capacitance or turbidity of the uninoculated growth medium or delectably decreased as compared to the impedance of the uninoculated growth medium.

5. The method of claim 4 wherein the nutrient component of said bacteriological medium comprises Brain Hear Infusion Broth.

6. The method of claim 4 wherein said fresh animal product is poultry.

7. The method of claim 6 wherein said fresh animal product is a chicken carcass or a part thereof.

8. The method of claim 4 wherein said fresh animal product is selected from the group consisting of beef, pork, veal, lamb, fish, shellfish, and dairy products.

9. A *Pseudomonas fluorescens* selective additive comprising Irgasan, carbonic film and nitrofurantoin in a ratio, by weight, of 25:120:4.

10. A method for the selection of *Pseudomonas fluorescens* from a sample comprising a mixture of bacteria, said method comprising the step of culturing a portion of said sample in the bacteriological growth medium of claim 1.

11. The method of claim 10, wherein the step of culturing is carried out in a bacteriological medium comprising Irgasan at a concentration from about 25 to about 30 µg/ml, carbenicillin at concentration from about 120 to about 130 µg/ml, and nitrofurantoin at a concentration from about 3 to about 20 µg/ml.

12. The method of claim 11 wherein the nutrient component of said bacteriological medium is Brain Heart Infusion Broth.

13. The method of claim 11 wherein the nutrient component of said bacteriological medium is Brain Heart Infusion Agar.

* * * * *

UNITED STATES PATENT AND TRADEMARK OFFICE
CERTIFICATE OF CORRECTION

PATENT NO.    : 5,741,663

DATED         : April 21, 1998

INVENTOR(S)   : Russell

It is certified that error appears in the above-identified patent and that said Letters Patent is hereby corrected as shown below:

In column 3, line 19, please delete "Court." and replace with --Coun--.
In column 3, line 38-39, please delete "Pseudomonas fluorescens" and replace with --Pseudomonas (fluorescens--.
In column 5, line 28, please delete "(BIB)" and replace with --(BHI)--.
In column 7, line 35, please delete "BIII" and replace with --BHI--.
In column 11, line 13, please delete "GAS" and replace with --CAS--.
In column 11, line 25, please delete "1 ml," and replace with --1 m L.
In column 11, line 39, please delete "*Food Protection*" and replace with --*J. Food Protection*--.
In column 12, line 55, please delete "ribrio" and replace with --Vibrio--.
In column 14, line 2, please delete "(bioMédrieux" and replace with --bioMérieux--.
In column 14, line 10, please delete "*Food Protection*" and replace with --*J. Food Protection*--.
In column 16, line 14, under column 1 of the table, please delete "30+" and replace with --30±--.
In column 17, line 29, under column 1 of the table, please delete "29+" and replace with --29±--.
In column 17, line 57, under column 1 of the table, please delete "51+" and replace with --51±--.
In column 17, line 60, please delete "Vbrio" and replace with --Vibrio--.
In column 25, line 17, please delete "carbonic film" and replace with --carbenicillin--.

Signed and Sealed this

Twenty-fifth Day of August, 1998

Attest:

BRUCE LEHMAN

*Attesting Officer*       Commissioner of Patents and Trademarks